United States Patent
Crnkovich et al.

(10) Patent No.: US 6,775,577 B2
(45) Date of Patent: Aug. 10, 2004

(54) METHOD AND SYSTEM FOR CONTROLLING A MEDICAL DEVICE

(75) Inventors: Martin J. Crnkovich, Walnut Creek, CA (US); Christian Schlaeper, Concord, CA (US); Scott N. Walker, Alamo, CA (US)

(73) Assignee: Fresenius USA, Inc., Lexington, MA (US)

( * ) Notice: Subject to any disclaimer, the term of this patent is extended or adjusted under 35 U.S.C. 154(b) by 362 days.

(21) Appl. No.: 09/908,334

(22) Filed: Jul. 18, 2001

(65) Prior Publication Data

US 2003/0018395 A1 Jan. 23, 2003

(51) Int. Cl.$^7$ .............................................. G05B 11/01
(52) U.S. Cl. ........................... 700/11; 700/12; 700/13; 700/17; 700/83; 345/418; 345/149; 345/420; 600/523; 600/300; 600/301; 210/134; 210/143; 210/739; 210/793; 340/3.71
(58) Field of Search .............................. 700/11, 12, 13, 700/17, 19, 20, 83; 340/3.71; 345/418, 419, 420; 600/523, 300, 301, 509, 525; 210/739, 134, 143, 793, 798, 646, 645

(56) References Cited

U.S. PATENT DOCUMENTS

| | | | |
|---|---|---|---|
| 5,181,521 A | * | 1/1993 | Lemelson ................... 600/549 |
| 5,609,770 A | | 3/1997 | Zimmerman et al. |
| 5,658,456 A | * | 8/1997 | Kenley et al. ................. 210/85 |
| 5,725,776 A | * | 3/1998 | Kenley et al. ............... 210/646 |
| 5,744,027 A | | 4/1998 | Connell et al. |
| 5,788,851 A | | 8/1998 | Kenley et al. |
| 5,807,256 A | * | 9/1998 | Taguchi et al. ............. 600/425 |
| 5,863,421 A | * | 1/1999 | Peter et al. .................. 210/134 |
| 6,463,320 B1 | * | 10/2002 | Xue et al. .................... 600/523 |

* cited by examiner

*Primary Examiner*—Ramesh Patel
(74) *Attorney, Agent, or Firm*—Gibson, Dunn & Crutcher LLP; Stanley J. Gradisar

(57) ABSTRACT

In a medical device, a Tx Clock Button is presented on a graphics display overlain with a touch screen which allows an operator to control multiple functions of the medical device. Various parts of Tx Clock Button may be displayed in different colors, and based on the state of treatment at a given time and in response to the operator touching Tx Clock Button, the colors may change to visually indicate a change in state. When the Tx Clock Button is touched for the first time after a new patient has been selected, multiple functions, times, displays, parameters, and alarms of the medical device are initiated. When the Tx Clock Button is touched for the second time, various ones of the multiple functions, times, displays, parameters, and alarms may be suspended. A third touch of the Tx Clock Button may resume the suspended items.

60 Claims, 4 Drawing Sheets

METHOD AND SYSTEM FOR CONTROLLING A MEDICAL DEVICE

FIELD OF THE INVENTION

This invention relates to medical devices, and more particularly, to a method and system for controlling multiple functions of a medical device with a single button.

DETAILED DESCRIPTION OF THE INVENTION

Figure 1:
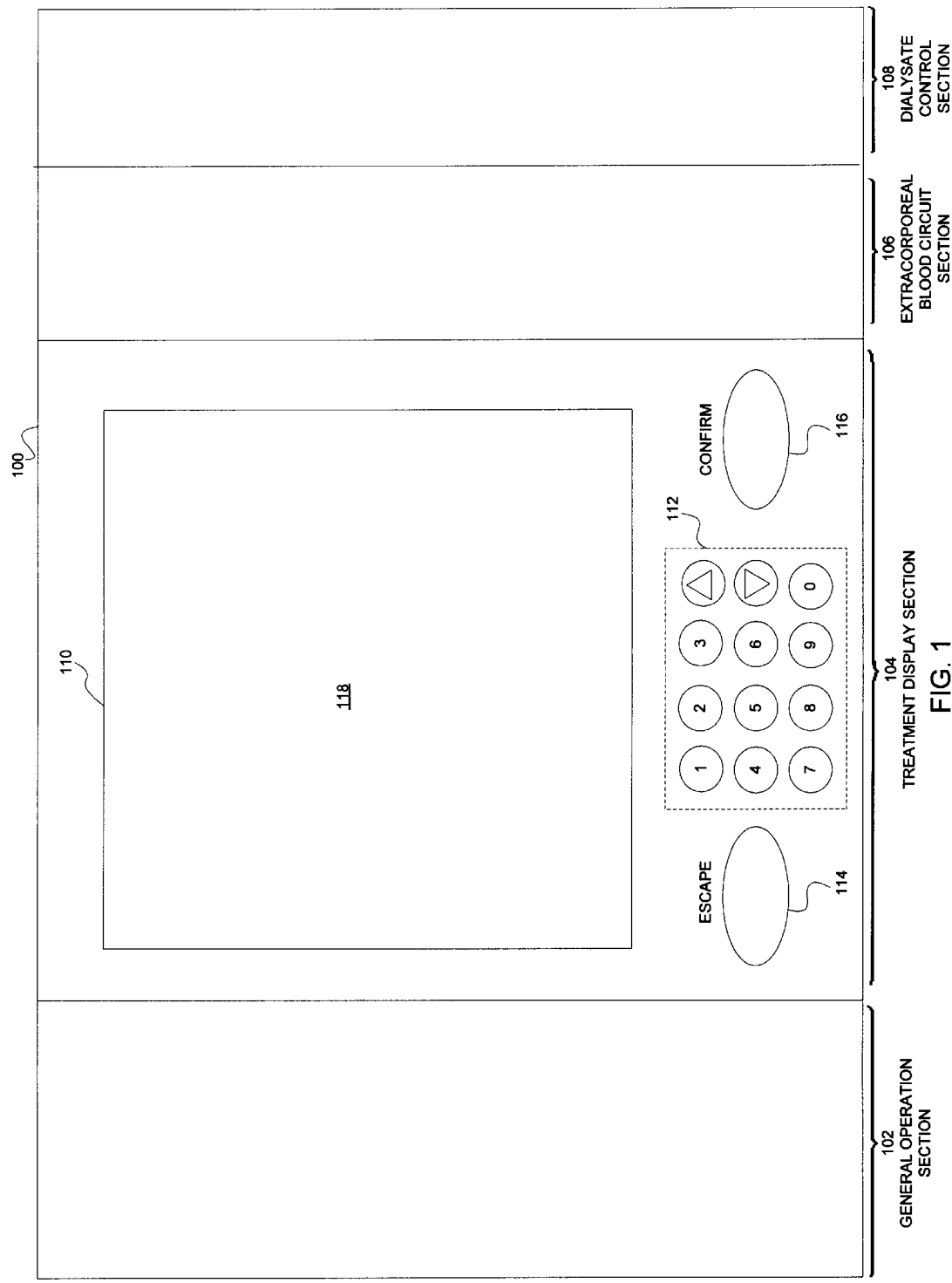
FIG. 1 shows a representation of a front control panel of a hemodialysis machine that incorporates the method and system for controlling multiple functions of a medical device with a single button of the present invention.

FIG. 1 shows a representation of a front control panel of a hemodialysis machine that incorporates the method and system for controlling multiple functions of a medical device with a single button of the present invention. Referring now to FIG. 1, in one embodiment of the invention, Front Control Panel 100 is located at the top and front of a hemodialysis machine, such as the Fresenius 2008K Model made by Fresenius USA, Inc., that contains the control keys an operator needs to operate the hemodialysis machine. Keys with related functions are grouped into four sections on Front Control Panel 100. The General Operation Section 102 has control keys (not shown in FIG. 1) associated with starting or stopping the basic power and alarm aspects of a dialysis treatment. General Operation Section 102 has control keys for turning the power on, muting or silencing an alarm, selecting a new patient (which erases the treatment information of the previous patient), and a reset for resetting alarms and for setting new arterial, venous, and transmembrane pressure (TMP).

Treatment Display Section 104 is located in the middle of Front Control Panel 100 and has Graphics Display 110 that is overlain with Touch Screen 118. Graphics Display 110 can display a variety of treatment screens through which the operator can use to set treatment parameters and monitor the treatment. Graphics Display 110 may be a CRT or an LCD type display. Touch Screen 118 allows operator input to set the treatment parameters and monitor the treatment and patient status during dialysis. The operator can access different treatment screens and set treatment parameters by touching Touch Screen 118 at specific identified areas graphically displayed as images of buttons or keys on Graphics Display 110. The terms "button" and "key" are used interchangeably herein, and may represent a physical button or key, or represent a displayed image of a button or key. Both physical buttons or keys and displayed images of buttons or keys that receive operator touch input send signals that are interpreted by the electronics of the hemodialysis machine. The touch input from the operator on the specific identified areas on Touch Screen 118 send signals which actuate the display of different treatment screens and set the treatment parameters. In one embodiment, most numbers and parameters selected on Touch Screen 118, or actions initiated on Touch Screen 118, must be confirmed by pressing the Confirm Key 116, which sends a signal that must be received in order to enable the previous signal to have its desired effect. This feature prevents a change in a treatment value if the touch screen is accidentally bumped. Other embodiments do not require the use of Confirm Key 116. Escape Key 114 is used to void the current entry and return to the previously entered parameter value. The other physical keys for operator input besides Escape Key 114 and Confirm Key 116 are the keys in Keypad 112, which are the number keys 0–9 and an up arrow key and a down arrow key. The number keys in Keypad 112 may be used to enter treatment parameter values for such treatment options as ultrafiltration rate, times, goal, and volumes, or for making selections inside a treatment screen displayed on Graphics Display 110. The up and down arrow keys may be used to scroll up or down a list of parameter choices or to increase or decrease parameter values. In another embodiment of the invention, Keypad 112, Escape Key 114, and Confirm Key 116 are graphically displayed as images of buttons or keys on Graphics Display 110 and actuated through Touch Screen 118. One skilled in the art will recognize that an infinite number of variations and combinations of physical buttons or keys and graphically displayed images of buttons or keys may be used in the present invention.

Extracorporeal Blood Circuit Section 106 contains keys and warning lights (not shown in FIG. 1) that are directly related to the transmission and monitoring of the patient's blood through an attached blood circuit unit (also not shown in FIG. 1).

Dialysate Control Section 108 contains the keys (not shown in FIG. 1) required to start and stop the flow of dialysate, the sodium variation system, and ultrafiltration pump.

Various components (not shown in FIG. 1) are located below Front Control Panel 100. The components, which may be modular components, non-modular components, or a combination of modular and non-modular components, may include an ultrafiltration pump, a blood pump, a blood pressure detector, a heparin pump, a level detector, a dialyzer, and the like.

Figure 2:
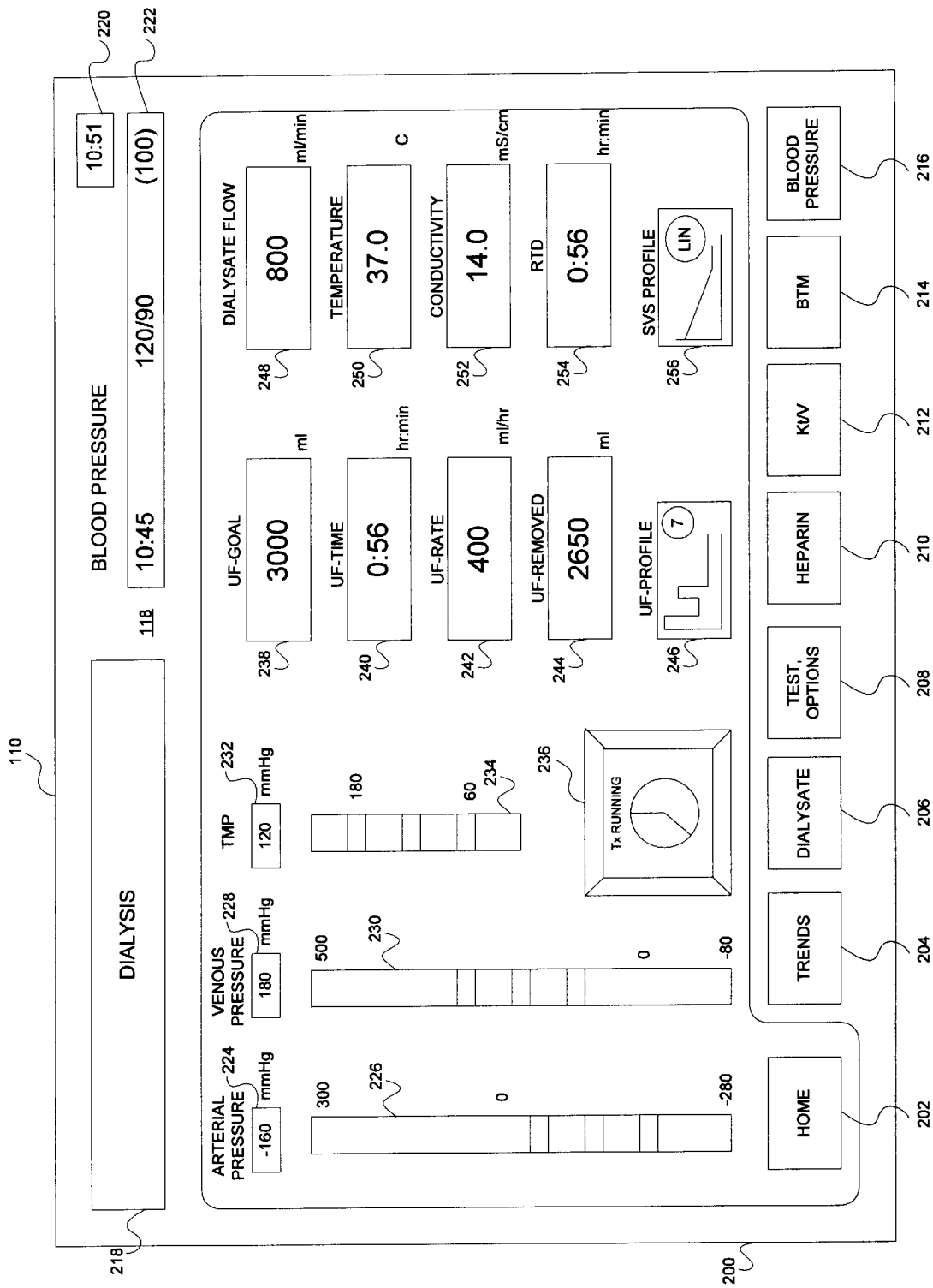
FIG. 2 shows a representation of a treatment screen in the graphics display in the front control panel of FIG. 1 of a hemodialysis machine that incorporates the method and system for controlling multiple functions of a medical device with a single button of the present invention.

FIG. 2 shows a representation of a treatment screen in the display in the front control panel of FIG. 1 of a hemodialysis machine that incorporates the method and system for controlling multiple functions of a medical device with a single button of the present invention. Referring now to FIG. 2, in one embodiment of the invention, screen access buttons 202, 204, 206, 208, 210, 212, 214, and 216 are used to access the various treatment screens through Touch Screen 118. As shown in FIG. 2, Home Access Button 202 has been touched, revealing Home Treatment Access Screen 200 displayed in Graphics Display 110. A different treatment access screen is displayed by pressing the different screen access buttons. Home Treatment Access Screen 200 provides a general overview of the status of the current treatment. The other treatment screens offer a more in-depth view of specific aspects of the current treatment, though some treatment screens may have some of the same information displayed as found on other treatment screens.

Status Box 218 appears at the top left corner of every treatment screen. During normal operation it displays the operation mode of the machine, which in this case is "Dialysis." During alarm situations, a warning message is displayed in Status Box 218. The message displayed in Status Box 218 may also prompt the operator for a specific action in situations when the treatment parameters are being set.

During normal treatment, Box 220 displays the current time and Box 222 displays the time of the last blood pressure reading and the patient's blood pressure and pulse rate at that time.

Arterial pressure in mmHg is displayed numerically in Meter Box 224, and graphically in Bar Graph 226. Similarly, venous pressure in mmHg is displayed numerically in Meter Box 228 and graphically in Bar Graph 230, and transmembrane pressure (TMP) in mmHg is displayed numerically in Meter Box 232 and graphically in Bar Graph 234.

Figure 3:
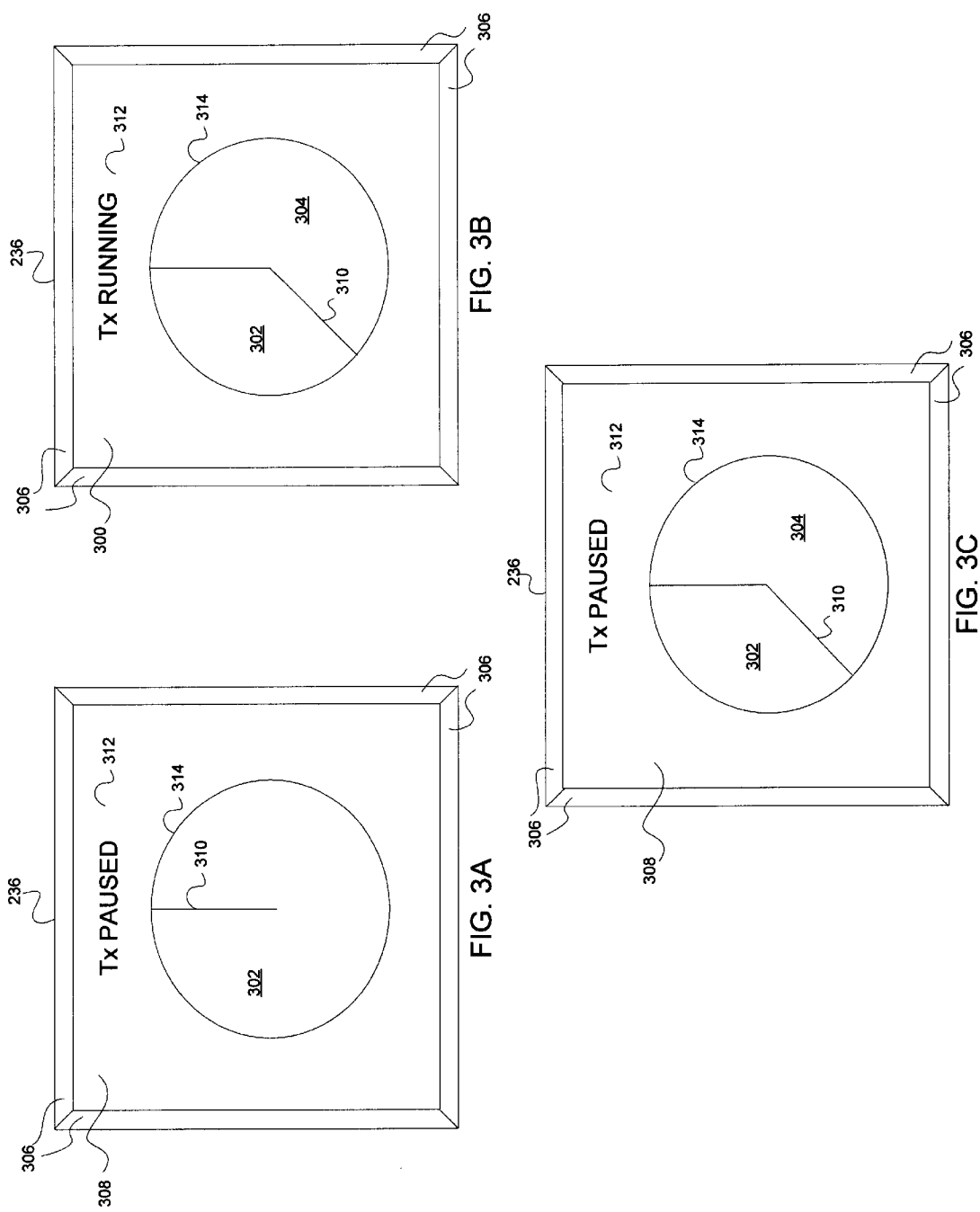
FIGS. 3A, 3B, and 3C show representations of a graphics display of the single button of FIG. 2 that incorporates the method and system for controlling multiple functions of a medical device of the present invention.

Tx Clock Button 236, more fully described in FIGS. 3A, 3B, and 3C, is touched to start, or to pause or suspend, the treatment. The terms "pause" and "suspend" are used interchangeably. Tx Clock Button 236 controls multiple functions of the hemodialysis machine when it is touched. In one embodiment, Tx Clock Button 236 must be touched in conjunction with Escape Key 114 or Confirm Key 116 (FIG. 1).

UF-Goal Button 238 displays the desired ultrafiltration (UF) in milliliters to be removed during the dialysis treatment. This is typically the difference between the patient's pre and dry weight plus saline or fluid intake during treatment. UF-Time Button 240 acts as a countdown timer displaying the remaining time in hours and minutes that ultrafiltration will be performed. The timer stops during a blood alarm or whenever the UF pump is stopped. During treatment, UF-Rate Button 242 displays the current rate of ultrafiltration in milliliters per hour. The rate ultrafiltration occurs is determined by the values entered in UF-Goal Button 238 and UF-Time Button 240 and the profile selected with UF-Profile Button 246. UF-Removed Button 244 keeps a running total in milliliters of the fluid drawn from the patient through ultrafiltration. When the value displayed in UF-Removed Button 244 is equal to the value entered in UF-Goal Button 238, an alarm sounds and the message, "UF GOAL REACHED" is displayed in Status Box 218. UF-Profile Button 246 when touched brings up the UF Profile Selection Screen. Once a profile is selected, and the operator pushes Home Access Button 202, the profile selected is displayed in UF-Profile Button 246.

Dialysate Flow Button 248 displays the current dialysate flow rate in milliliters per minute. Temperature Button 250 displays the current temperature in degrees centigrade of the dialysate. Pressing Temperature Button 250 allows the operator to set the desired temperature, and thereafter the actual temperature is displayed. If the temperature varies too far from the set point, an alarm sounds, a warning message is displayed in Status Box 218, and the dialysate goes into bypass. Conductivity Button 252 displays the current conductivity in millisiemens per centimeter of the dialysate. RTD (Remaining Time of Dialysis) Button 254 acts as a countdown timer displaying the amount of treatment time remaining. At the end of treatment (RTD=0:00) an alarm sounds and the message "RTD ZERO" is displayed in Status Box 218.

SVS Profile Button 256 when touched brings up the Sodium Variation System (SVS) Profile Selection Screen. Once a profile is selected, and the operator pushes Home Access Button 202, the profile selected is displayed in SVS Profile Button 256.

FIGS. 3A, 3B, and 3C show representations of a screen display of the single button of FIG. 2 that incorporates the method and system for controlling multiple functions of a medical device of the present invention. Referring now to FIGS. 3A, 3B, and 3C, Tx Clock Button 236 is shown in various stages of use. Various parts of Tx Clock Button 236 may be displayed in different colors, and based on the state of treatment at a given time and in response to the operator touching Tx Clock Button 236, the colors may change to visually indicate a change in state. The colors stated in the description below are exemplary for one embodiment of the invention. One skilled in the art will recognize that many different colors and color changes could be used for the various parts of Tx Clock Button 236. Though Tx Clock 314 in FIGS. 3A–3C is shown circular with Hand 310 sweeping in a clock-like fashion, one skilled in the art will recognize that other shapes, and other dividers, like Hand 310, with different movements are possible. For example, Tx Clock 314 may be shaped like a bar graph where a divider moves in a lateral fashion along the length of the bar and separates two rectangular segments of the bar, one segment representing the time of treatment remaining and the other segment representing the time of treatment elapsed.

FIG. 3A shows Tx Clock Button 236 at the beginning of treatment. Hand 310 in Tx Clock 314 is displayed as a green colored line, and Time Remaining Segment 302 is white. Status Indicator 312 displays "Tx Paused." In an embodiment where Tx Clock Button 236 must be touched in conjunction with Escape Key 114 or Confirm Key 116 (FIG. 1), when an operator presses Tx Clock Button 236, Perimeter Area 306 turns dark blue. Once Escape Key 114 or Confirm Key is touched, Perimeter Area 306 changes back to its previous color of light blue.

When Tx Clock Button 236 is touched for the first time after a new patient has been selected with the control keys of General Operation Section 102 (FIG. 1), multiple functions of the hemodialysis machine are initiated. In addition, one or more timers begin to accumulate times of operation and various parameters begin to be accumulated. In one embodiment of the invention, the following items are initiated when Tx Clock Button 236 is touched for the first time: 1) the On Line Clearance (OLC) schedule is established; 2) if a SVS profile has been selected, the SVS program begins and the SVS LED is turned on; 3) if a UF rate has been set above zero, the UF pump and LED turn on and the UF timer beings to count, and the UF time transfers to RTD if the UF volume is equal to zero; 4) the Blood Volume Monitor (BVM) is enabled, parameters are initialized, and the first relative blood volume measurement is taken; 5) the Blood Temperature Module (BTM) is enabled; 6) the trends screen, the OLC screen, and the Blood Temperature Module (BTM) screen begin; 7) the clearance test is enabled; and 8) the dialysate sampler is enabled. Also, pressing Tx Clock Button 236 turns the Tx Clock 314 on, Hand 310 will begin to move as time elapses, and Status Indicator 312 displays "Tx Running" as shown in FIG. 3B. The following functions and/or times are also started and begin to accumulate: 1) SVS time; 2) UF time; 3) heparin pump infusion time; 4) RTD time; and 5) Kt/V time. Kt/V is a formula for prescribing adequate dialysis and checking to see if the patient is receiving enough dialysis. Kt/V is calculated by multiplying the rate at which toxins are removed, called clearance (K), by the amount of time (t) of the dialysis treatment, and dividing by the distribution volume (V) of the removed toxins under consideration in the body—which may be the volume of water in the body. The accumulation of Kt could be used instead of Kt/V. Any ultrafiltration is not counted unless Tx Clock 314 is running as indicated by Status Indicator 312 displaying "Tx RUNNING."

Time Remaining Segment 302 decreases in area and Time Elapsed Segment 304 increases in area, and Hand 310 moves in proportion to the time elapsed versus the total time as the treatment progresses to completion. The time to fill Time Elapsed Segment 304 is the cumulative RTD time. If the RTD is increased during the treatment, the Time Remaining Segment 302 and Time Elapsed Segment 304 are rescaled to account for the increased time. Time Elapsed Segment 304 is displayed in green and represents the amount of treatment completed. When treatment is completed, RTD is equal to zero, Time Remaining Segment 302 disappears, and Time Elapsed Segment 304 is a completely green circle.

Pressing Tx Clock Button 236 when Status Indicator 312 displays "Tx RUNNING" and before RTD has been completed interrupts treatment and Status Indicator 312 displays "Tx PAUSED" as shown in FIG. 3C. In such a state, some functions of the medical device are suspended, some time accumulations are suspended, and some parameter accumulations are suspended. In one embodiment of the invention when treatment is paused, or suspended, in this manner the following events or conditions are initiated: 1) Time Elapsed Segment 304 and Hand 310 turn from green to yellow; 2) if active, the SVS time stops, the SVS LED flashes, and the conductivity remains at the current value; 3) the UF pump and LED turn off and the UF-Time Button 240 stops counting down; 4) RTD Button 254 stops counting down; 5) the heparin pump and LED turn off and the heparin pump infusion time stops; 6) BTM parameters are suspended; 7) Blood Volume Processed (BVP) is not accumulated; 8) dialysate sampler volume does not accumulate; 9) the profile trend graphs, BTM graph, OLC graph, and blood pressure graph pause; 10) OLC test is not allowed; and 11) automatically scheduled blood pressure tests are not taken and the blood pressure interval is suspended. The sodium content of the dialysate remains at the profile level it was when the treatment was paused. The blood pump and the dialysate flow, however, remain running. If blood is sensed when the Tx Clock Button 236 is paused, an advisory message, "Tx Clock Paused," is displayed in Status Box 218. After one minute an audible alert is sounded.

Current medical devices have the ability to be switched to a bypass mode. Ultrafiltration typically continues in such devices and blood is still flowing. However, current devices lack the functionality of Tx Clock Button 236 of the present invention.

Each time Tx Clock Button 236 is subsequently touched, turning to "Tx RUNNING" while blood is sensed, some or all of the suspended functions, time accumulations, and parameter accumulations are resumed. In one embodiment of the invention, the following functions, times, and/or parameters are started, resumed, or are initiated: 1) the SVS time accumulates if a SVS profile has been selected; 2) if a UF rate has been set above zero, the UF pump and LED turn on and the UF time accumulates, 3) if the heparin pump rate has been set above zero, the heparin pump and LED turn on and the heparin pump infusion time accumulates; 4) RTD begins to decrement; 5) UF-Goal button 238, UF-Time Button 240, UF-Rate Button 242, and UF-Removed Button 244 become active; 5) BTM parameters are active; 6) BVP is accumulated; 7) dialysate sampler volume counts; 8) trend screen graphing continues; 9) OLC test is allowed, and 10) automatically scheduled blood pressure test is allowed.

If no blood is sensed when Tx Clock Button 236 is turned to "Tx RUNNING" a message is displayed in Status Box 218 such as "NEED BLOOD SENSED" or "BLOOD NOT PRESENT IN VENOUS LINE." After about one minute, an audible warning is sounded. One skilled in the art will recognize that other types of medical devices besides hemodialysis machines may incorporate the Tx Clock Button 236 as a method and system for controlling the medical device. Such devices include, but are not limited to, peritoneal dialysis devices, blood cell separation devices, and blood adsorption devices. One skilled in the art will recognize that Tx Clock Button 236 may also be a physical key or button which when pressed sends signals to actuate the functionality described above. In such a case, the various graphic displays currently within Tx Clock Button 236 could be displayed on a portion of Graphics Display 110. The operator touch input on the physical key or button causes an electrical connection that sends a signal comparable to the signal sent by touching Touch Screen 118 where Tx Clock Button 236 is displayed.

Figure 4:
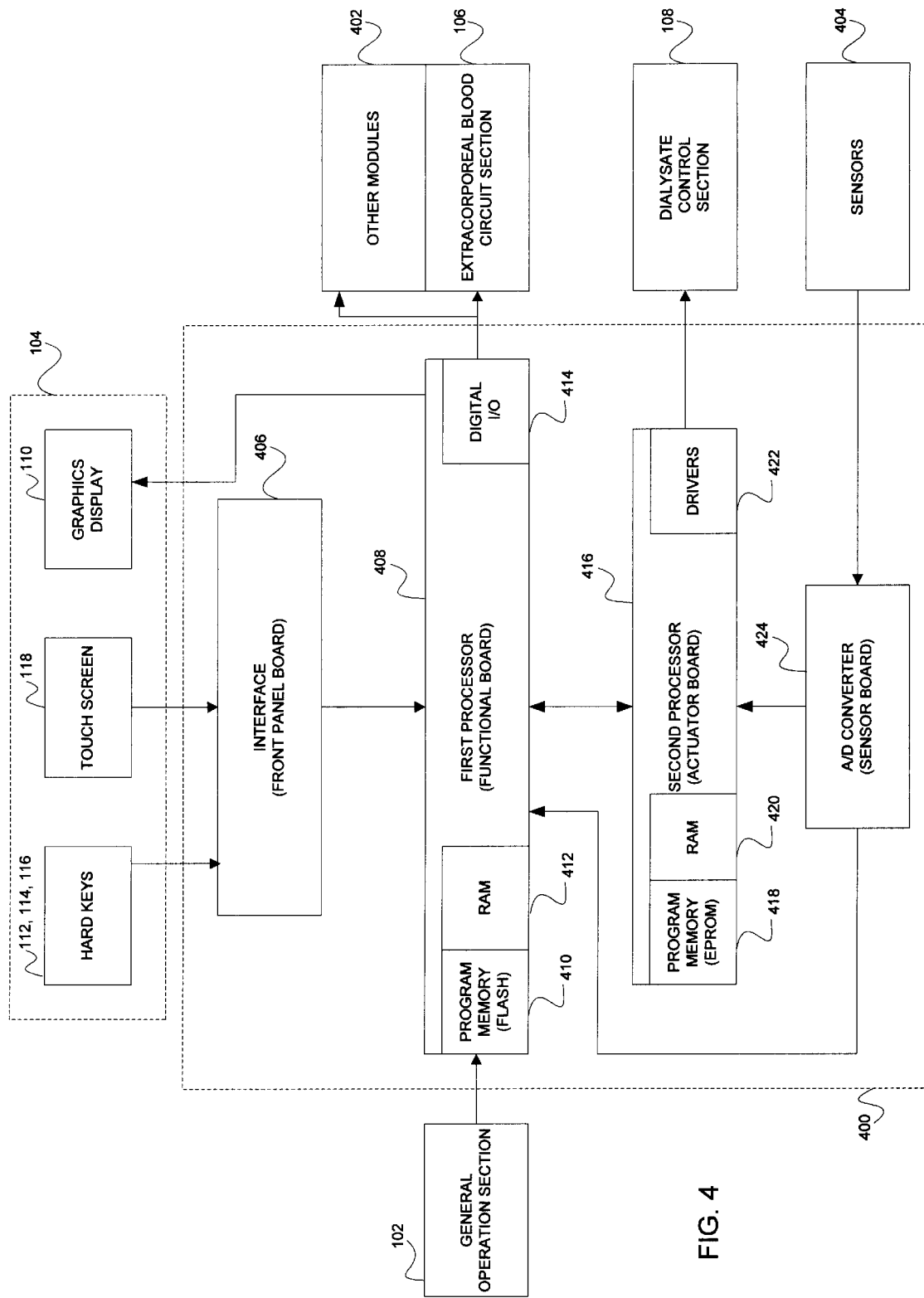
FIG. 4 shows a functional block diagram of the overall system of the hemodialysis machine of FIGS. 1 and 2 that incorporates the system for controlling multiple functions of a medical device with a single button of the present invention.

FIG. 4 shows a functional block diagram of the overall system of the hemodialysis machine of FIGS. 1 and 2 that incorporates the system for controlling multiple functions of a medical device with a single button of the present invention. Referring now to FIG. 4, in one embodiment of the invention, Control Unit 400 has Interface 406, which is the front panel board that receives input from Treatment Display Section 104. Input from the hard keys, which includes Keypad 112, Escape Key 114, and Confirm Key 116, and Touch Screen 118, are received and passed to First Processor 408, which is on a functional board. First Processor 408 may be a CPU (Central Processing Unit), a microprocessor (a CPU on a single chip), or any other type of processing device. In this embodiment, First Processor 408 is the interface and master control CPU for the hemodialysis machine. First Processor 408 controls Extracorporeal Blood Circuit 106 and Other Modules 402 that are connected to the hemodialysis machine. First Processor 408 also receives input from General Operation Section 102. First Processor 408 has RAM 412 and Program Memory 410, which in one embodiment is flash memory. Programming code for the user interface, the touch screen controller, and the overall general operations of Control Unit 400 reside in First Processor 408. Digital I/O 414 also resides on First Processor 408. First Processor 408 sends signals to control Graphics Display 110.

First Processor 408 is in communication with Second Processor 416, which is on an actuator board. Second Processor 416 may also be a CPU (Central Processing Unit), a microprocessor (a CPU on a single chip), or any other type of processing device. Second Processor 416 controls the Drivers 422 for Dialysate Control Section 108, the fluid control, and the mixing of the dialysate solution. Second Processor 416 has RAM 420 and Program Memory 418, which resides in an EPROM in one embodiment or an EEPROM in another embodiment. One skilled in the art will recognize that First Processor 408 and Second Processor 416 may be combined into one processor, or comprise more processors than those shown in FIG. 4.

Sensors 404 feed back into A/D Converter 424, which is on a sensor board. A/D Converter 424 also communicates with First Processor 408, thus providing redundant monitoring.

Having described the present invention, it will be understood by those skilled in the art that many changes in construction and circuitry and widely differing embodiments and applications of the invention will suggest themselves without departing from the scope of the present invention.

What is claimed is:

1. A method for controlling multiple functions of a medical device, the method comprising:
receiving a first operator input on a button of the medical device, wherein said first operator input on said button actuates,
starting at least one function of the medical device;
starting at least two time accumulations of the medical device; and
starting accumulation of at least two parameters of the medical device.

2. A method according to claim 1 further comprising:
receiving a second operator input on said button, wherein said second operator input on said button actuates,
suspending at least one of said at least one function of the medical device;
suspending at least one of said at least two time accumulations of the medical device; and
suspending said accumulation of at least one of said at least two parameters of the medical device.

3. A method according to claim 2 further comprising:
receiving a third operator input on said button, wherein said third operator input on said button actuates,
resuming said suspended said at least one of said at least one function of the medical device;
resuming said suspended said at least one of said at least two time accumulations of the medical device; and
resuming said suspended said accumulation of at least one of said at least two parameters of the medical device.

4. A method according to claim 3 wherein said first operator input, said second operator input, and said third operator input must be followed by an operator confirm key input before said actuation occurs.

5. A method according to claim 1 wherein said button comprises a button image displayed on a graphics display of the medical device, wherein said graphics display is overlain with a touch screen for receiving touch input from an operator, such as said first operator input on said button image displayed on said graphics display.

6. A method according to claim 1 wherein said first operator input on said button further actuates:
displaying graphically on a graphics display of the medical device a progress of treatment time;
enabling a first alarm function of the medical device; and
enabling a first control function of the medical device.

7. A method according to claim 6 further comprising:
receiving a second operator input on said button, wherein said second operator input on said button actuates,
displaying graphically on said graphics display a pause of said progress of treatment time;
enabling a second alarm function of the medical device; and
enabling a second control function of the medical device.

8. A method according to claim 7 further comprising:
receiving a third operator input on said button, wherein said third operator input on said button actuates,
redisplaying graphically on said graphics display said progress of treatment time;
re-enabling said first alarm function of the medical device; and
re-enabling said first control function of the medical device.

9. A method according to claim 8 wherein said first operator input, said second operator input, and said third operator input must be followed by an operator confirm key input before said actuation occurs.

10. A method according to claim 9 wherein said button comprises a button image displayed on said graphics display, wherein said graphics display is overlain with a touch screen for receiving touch input from an operator, such as said first operator input, said second operator input, and said third operator input on said button image displayed on said graphics display, and further wherein said progress of treatment time, said pause of said progress of treatment time, and said redisplaying of said progress of treatment time are displayed on said graphics display within said button image.

11. A method according to claim 6 wherein said displaying graphically said progress of treatment time further comprises:
displaying a time remaining segment in a first color that proportionally decreases in area as said progress of treatment time elapses; and
displaying a time elapsed segment in a second color that proportionally increases in area as said progress of treatment time elapses.

12. A method according to claim 11 wherein said time remaining segment and said time elapsed segment are displayed as pie-shaped segments.

13. A method according to claim 11 wherein said time remaining segment and said time elapsed segment are displayed as rectangular bar graph-shaped segments.

14. A method according to claim 6 wherein the medical device comprises a hemodialysis machine.

15. A method according to claim 14 wherein said first alarm function further comprises sounding an audible alarm if no blood is sensed in a blood circuit of said hemodialysis machine when said progress of treatment time is graphically displayed as running.

16. A method according to claim 14 wherein said first control function further comprises allowing automatic blood pressure measurements when said progress of treatment time is graphically displayed as running.

17. A method according to claim 14 wherein said second alarm function further comprises sounding an audible alarm if blood is sensed in a blood circuit of said hemodialysis machine when said progress of treatment time is graphically displayed as paused.

18. A method according to claim 14 wherein said at least one function of said hemodialysis machine comprises at least one of an ultrafiltration pump, a blood pump, a blood pressure detector, a heparin pump, a level detector, and a dialyzer.

19. A method according to claim 14 wherein said at least two time accumulations of said hemodialysis machine comprise at least two of a remaining time of dialysis time, a sodium variation system time, an ultrafiltration time, a heparin pump time, and a Kt/V time.

20. A method according to claim 14 wherein said at least two parameters of said hemodialysis machine comprise at least two of a Kt/V, a blood temperature, an ultrafiltration volume accumulated, a heparin volume accumulated, a blood pressure, a blood volume processed, and a clearance test.

21. A system for controlling multiple functions of a medical device, the system comprising:
a button for receiving operator input and sending an operator input signal;
a processor, connectable to said button for receiving said operator input signal, said processor having,
a memory; and
a program code stored in said memory;

wherein said processor running said program code interprets said operator input signal and outputs control signals; and at least one component of the medical device in communication with said processor;

wherein a first operator input signal is interpreted by said processor and outputs a first plurality of control signals that, start said at least one component of the medical device;

start at least two time accumulations of the medical device; and start accumulation of at least two parameters of the medical device.

22. The system according to claim 21 wherein a second operator input signal is interpreted by said processor and outputs a second plurality of control signals that, suspend at least one of said at least one component of the medical device;

suspend at least one of said at least two time accumulations of the medical device; and suspend said accumulation of at least one of said at least two parameters of the medical device.

23. The system according to claim 22 wherein a third operator input signal is interpreted by said processor and outputs a third plurality of control signals that, resume said suspended said at least one of said at least one component of the medical device;

resume said suspended at least one of said at least two time accumulations of the medical device; and resume said suspended said accumulation of at least one of said at least two parameters of the medical device.

24. The system according to claim 23 further comprising:

a confirm key connectable to said processor for receiving operator confirm input and sending an operator confirm input signal, wherein said output control signals associated with said first operator input signal, said second operator input signal, and said third operator input signal must be followed by said operator confirm input signal before said output control signals are output by said processor.

25. The system according to claim 21 further comprising:

a graphics display of the medical device in communication with said processor;

a touch screen overlaying said graphics display in communication with said processor for receiving touch input from an operator;

wherein said program code further comprises,
a touch screen controller; and
a user interface;
wherein said button comprises a button image displayed on said graphics display of the medical device, wherein said touch screen receives touch input from an operator, such as said first operator input on said button image displayed on said graphics display, and sends said operator input signal.

26. The system according to claim 21 further comprising:

a graphics display of the medical device in communication with said processor;

wherein said first plurality of control signals additionally, cause said graphics display to display graphically a progress of treatment time;

enable a first alarm function of the medical device; and enable a first control function of the medical device.

27. The system according to claim 26 wherein a second operator input signal interpreted by said processor outputs a second plurality of control signals that, cause said graphics display to display graphically a pause of said progress of treatment time;

enable a second alarm function of the medical device; and enable a second control function of the medical device.

28. The system according to claim 27 wherein a third operator input signal interpreted by said processor outputs a third plurality of control signals that, cause said graphics display to redisplay graphically said progress of treatment time;

re-enable said first alarm function of the medical device; and re-enable said first control function of the medical device.

29. The system according to claim 28 wherein said output control signals associated with said first operator input signal, said second operator input signal, and said third operator input signal must be followed by said operator confirm input signal before said output control signals are output by said processor.

30. The system according to claim 29 further comprising:

a touch screen overlaying said graphics display in communication with said processor for receiving touch input from an operator;

wherein said program code further comprises,
a touch screen controller; and
a user interface;
wherein said button comprises a button image displayed on said graphics display, wherein said touch screen receives touch input from an operator, such as said first operator input, said second operator input, and said third operator input on said button image displayed on said graphics display, and further wherein said progress of treatment time, said pause of said progress of treatment time, and said redisplaying of said progress of treatment time are displayed on said graphics display within said button image.

31. The system according to claim 21 wherein the medical device comprises a hemodialysis machine.

32. The system according to claim 31 wherein said at least one component of said hemodialysis machine comprises at least one of an ultrafiltration pump, a blood pump, a blood pressure detector, a heparin pump, a level detector, and a dialyzer.

33. The system according to claim 31 wherein said at least two time accumulations of said hemodialysis machine comprise at least two of a remaining time of dialysis time, a sodium variation system time, an ultrafiltration time, a heparin pump time, and a Kt/V time.

34. The system according to claim 31 wherein said at least two parameters of said hemodialysis machine comprise at least two of a Kt/V, a blood temperature, an ultrafiltration volume accumulated, a heparin volume accumulated, a blood pressure, a blood volume processed, and a clearance test.

35. A method for controlling multiple functions of a medical device, the method comprising:

receiving an operator input on a button of the medical device, wherein said operator input on said button actuates, suspending at least one of at least one function of the medical device;

suspending at least one of at least two time accumulations of the medical device; and suspending accumulation of at least one of at least two parameters of the medical device.

36. A method according to claim 35 further comprising:
receiving a next operator input on said button after said operator input, wherein said next operator input on said button actuates,
resuming said suspended said at least one of said at least one function of the medical device;
resuming said suspended said at least one of said at least two time accumulations of the medical device; and
resuming said suspended said accumulation of at least one of said at least two parameters of the medical device.

37. A method according to claim 36 wherein said operator input and said next operator input must be followed by an operator confirm key input before said actuation occurs.

38. A method according to claim 35 wherein said button comprises a button image displayed on a graphics display of the medical device, wherein said graphics display is overlain with a touch screen for receiving touch input from an operator, such as said operator input on said button image displayed on said graphics display.

39. A method according to claim 35 wherein said operator input on said button further actuates:
displaying graphically on a graphics display of the medical device a pause in a progress of treatment time;
enabling an alarm function of the medical device; and
enabling a control function of the medical device.

40. A method according to claim 39 further comprising:
receiving a next operator input on said button after said operator input, wherein said next operator input on said button actuates,
displaying graphically on said graphics display a resumption in said progress of treatment time;
enabling a second alarm function of the medical device; and
enabling a second control function of the medical device.

41. A method according to claim 40 wherein said operator input and said next operator input must be followed by an operator confirm key input before said actuation occurs.

42. A method according to claim 41 wherein said button comprises a button image displayed on said graphics display, wherein said graphics display is overlain with a touch screen for receiving touch input from an operator, such as said operator input and said next operator input on said button image displayed on said graphics display, and further wherein said pause of said progress of treatment time and said resumption of said progress of treatment time are displayed on said graphics display within said button image.

43. A method according to claim 39 wherein the medical device comprises a hemodialysis machine.

44. A method according to claim 43 wherein said second alarm function further comprises sounding an audible alarm if blood is sensed in a blood circuit of said hemodialysis machine when said progress of treatment time is graphically displayed as paused.

45. A method according to claim 43 wherein said at least one function of said hemodialysis machine comprises at least one of an ultrafiltration pump, a blood pump, a blood pressure detector, a heparin pump, a level detector, and a dialyzer.

46. A method according to claim 43 wherein said at least two time accumulations of said hemodialysis machine comprise at least two of a remaining time of dialysis time, a sodium variation system time, an ultrafiltration time, a heparin pump time, and a Kt/V time.

47. A method according to claim 43 wherein said at least two parameters of said hemodialysis machine comprise at least two of a Kt/V, a blood temperature, an ultrafiltration volume accumulated, a heparin volume accumulated, a blood pressure, a blood volume processed, and a clearance test.

48. A system for controlling multiple functions of a medical device, the system comprising:
a button for receiving operator input and sending an operator input signal;
a processor, connectable to said button for receiving said operator input signal, said processor having,
a memory; and
a program code stored in said memory;
wherein said processor running said program code interprets said operator input signal and outputs control signals; and
at least one component of the medical device in communication with said processor;
wherein an operator input signal is interpreted by said processor and outputs a plurality of control signals that,
suspend at least one of said at least one component of the medical device;
suspend at least one of at least two time accumulations of the medical device; and
suspend accumulation of at least one of at least two parameters of the medical device.

49. The system according to claim 48 wherein a next operator input signal after said operator input signal is interpreted by said processor and outputs a next plurality of control signals that,
resume said suspended said at least one of said at least one component of the medical device;
resume said suspended at least one of said at least two time accumulations of the medical device; and
resume said suspended said accumulation of at least one of said at least two parameters of the medical device.

50. The system according to claim 49 further comprising:
a confirm key connectable to said processor for receiving operator confirm input and sending an operator confirm input signal,
wherein said output control signals associated with said operator input signal and said next operator input signal must be followed by said operator confirm input signal before said output control signals are output by said processor.

51. The system according to claim 48 further comprising:
a graphics display of the medical device in communication with said processor;
a touch screen overlaying said graphics display in communication with said processor;
wherein said program code further comprises,
a touch screen controller; and
a user interface;
wherein said button comprises a button image displayed on said graphics display of the medical device, wherein said touch screen receives touch input from an operator, such as said first operator input on said button image displayed on said graphics display, and sends said operator input signal.

52. The system according to claim 48 further comprising:
a graphics display of the medical device in communication with said processor.

53. The system according to claim 52 wherein said plurality of control signals additionally,
- cause said graphics display to display graphically a pause of said progress of treatment time;
- enable an alarm function of the medical device; and
- enable a control function of the medical device.

54. The system according to claim 53 wherein a next operator input signal after said operator input signal is interpreted by said processor and outputs a next plurality of control signals that,
- cause said graphics display to display graphically a resumption in said progress of treatment time;
- enable a second alarm function of the medical device; and
- enable a second control function of the medical device.

55. The system according to claim 54 wherein said output control signals associated with said operator input signal and said next operator input signal must be followed by said operator confirm input signal before said output control signals are output by said processor.

56. The system according to claim 55 further comprising:
- a touch screen overlaying said graphics display in communication with said processor for receiving touch input from an operator;
- wherein said program code further comprises,
  - a touch screen controller; and
  - a user interface;
    - wherein said button comprises a button image displayed on said graphics display, wherein said touch screen receives touch input from an operator, such as said operator input on said button image displayed on said graphics display, and sends said operator input signal and said next operator input signal, and further wherein said pause of said progress of treatment time, and said resumption of said progress of treatment time are displayed on said graphics display within said button image.

57. The system according to claim 48 wherein the medical device comprises a hemodialysis machine.

58. The system according to claim 57 wherein said at least one component of said hemodialysis machine comprises at least one of an ultrafiltration pump, a blood pump, a blood pressure detector, a heparin pump, a level detector, and a dialyzer.

59. The system according to claim 57 wherein said at least two time accumulations of said hemodialysis machine comprise at least two of a remaining time of dialysis time, a sodium variation system time, an ultrafiltration time, a heparin pump time, and a Kt/V time.

60. The system according to claim 57 wherein said at least two parameters of said hemodialysis machine comprise at least two of a Kt/V, a blood temperature, an ultrafiltration volume accumulated, a heparin volume accumulated, a blood pressure, a blood volume processed, and a clearance test.

* * * * *

UNITED STATES PATENT AND TRADEMARK OFFICE
CERTIFICATE OF CORRECTION

PATENT NO. : 6,775,577 C1  Page 1 of 1
APPLICATION NO. : 90/009248
DATED : March 23, 2010
INVENTOR(S) : Martin Joseph Crnkovich It is certified that error appears in the above-identified patent and that said Letters Patent is hereby corrected as shown below:

Claim 7, column 3, line 9:
    delete "operator on" and replace with --operator input on--.

Claim 47, column 4, line 46-47:
    delete "comprises" and replace with --comprise--.

Claim 64, column 5, line 62:
    delete "comprises" and replace with --comprise--.

Claim 75, column 6, line 57:
    delete "and," and replace with --and--.

Claim 110, column 10, line 27:
    delete "acutation" and replace with --actuation--.

Claim 129, column 12, line 32:
    delete "paramters" and replace with --parameters--.

Signed and Sealed this

First Day of June, 2010

David J. Kappos
*Director of the United States Patent and Trademark Office*

(12) EX PARTE REEXAMINATION CERTIFICATE (7417th)
United States Patent
Crnkovich et al.

(10) Number: US 6,775,577 C1
(45) Certificate Issued: Mar. 23, 2010

(54) METHOD AND SYSTEM FOR CONTROLLING A MEDICAL DEVICE

(75) Inventors: Martin J. Crnkovich, Walnut Creek, CA (US); Christian Schlaeper, Concord, CA (US); Scott N. Walker, Alamo, CA (US)

(73) Assignee: Fresenius USA, Inc., Lexington, MA (US)

Reexamination Request:
No. 90/009,248, Aug. 11, 2008

Reexamination Certificate for:
Patent No.: 6,775,577
Issued: Aug. 10, 2004
Appl. No.: 09/908,334
Filed: Jul. 18, 2001

(51) Int. Cl.
*G05B 23/02* (2006.01)
*G05B 15/02* (2006.01)

(52) U.S. Cl. .................. 700/11; 210/134; 210/143; 210/739; 210/793; 340/3.71; 345/418; 345/420; 600/300; 600/301; 600/523; 700/12; 700/13; 700/17; 700/83

(58) Field of Classification Search .................. None
See application file for complete search history.

(56) References Cited

U.S. PATENT DOCUMENTS

| | | | |
|---|---|---|---|
| 3,754,649 A | 8/1973 | Palubniak et al. | |
| 3,946,731 A | 3/1976 | Lichtenstein et al. | |
| 4,098,274 A | 7/1978 | Ebling et al. | |
| 4,153,554 A | 5/1979 | von der Heide et al. | |
| 4,370,983 A | 2/1983 | Lichtenstein et al. | |
| 4,601,830 A | 7/1986 | Chen | |
| 4,629,015 A | 12/1986 | Fried et al. | |
| 4,696,671 A | 9/1987 | Epstein et al. | |
| 4,718,022 A | 1/1988 | Cochran | |
| 4,731,731 A | 3/1988 | Cochran | |
| 4,739,492 A | 4/1988 | Cochran | |
| 4,756,706 A | 7/1988 | Kerns | |
| 4,796,634 A | 1/1989 | Huntsman et al. | |
| 4,827,430 A | 5/1989 | Aid et al. | |
| 4,898,578 A | 2/1990 | Rubalcaba | |
| 4,914,624 A | 4/1990 | Dunthorn | |
| 4,984,575 A | 1/1991 | Uchivama et al. | |
| 4,990,258 A | 2/1991 | Bjare et al. | |
| 4,991,193 A | 2/1991 | Cecil et al. | |
| 5,004,459 A | 4/1991 | Peabody et al. | |
| 5,054,774 A | 10/1991 | Belsito | |
| 5,056,059 A | 10/1991 | Tivig et al. | |
| 5,059,167 A | 10/1991 | Lundquist et al. | |
| 5,069,668 A | 12/1991 | Boydman | |
| 5,189,609 A | 2/1993 | Tivig et al. | |

(Continued)

FOREIGN PATENT DOCUMENTS

| | | |
|---|---|---|
| EP | 0 623 357 | 11/1994 |
| EP | 0 952 540 | 10/1999 |
| EP | 0 668 793 | 4/2000 |
| WO | WO 02/07796 | 1/2002 |

OTHER PUBLICATIONS

Operator's Instructions—Fresenius 90/2 Peritoneal Therapy Cycler (1991).

(Continued)

*Primary Examiner*—Lynne H Browne

(57) ABSTRACT

In a medical device, a Tx Clock Button is presented on a graphics display overlain with a touch screen which allows an operator to control multiple functions of the medical device. Various parts of Tx Clock Button may be displayed in different colors, and based on the state of treatment at a given time and in response to the operator touching Tx Clock Button, the colors may change to visually indicate a change in state. When the Tx Clock Button is touched for the first time after a new patient has been selected, multiple functions, times, displays, parameters, and alarms of the medical device are initiated. When the Tx Clock Button is touched for the second time, various ones of the multiple functions, times, displays, parameters, and alarms may be suspended. A third touch of the Tx Clock Button may resume the suspended items.

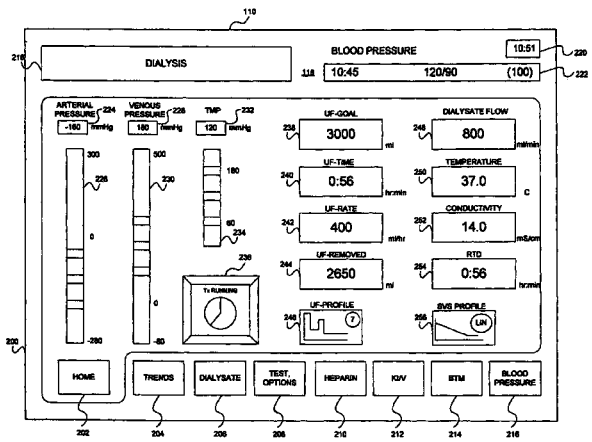

U.S. PATENT DOCUMENTS

| | | | |
|---|---|---|---|
| 5,247,434 A | 9/1993 | Peterson et al. | |
| 5,276,611 A | 1/1994 | Ghiraldi | |
| 5,324,422 A | 6/1994 | Colleran et al. | |
| 5,326,476 A | 7/1994 | Grogan et al. | |
| 5,421,823 A | 6/1995 | Kamen et al. | |
| 5,438,510 A | 8/1995 | Bryant et al. | |
| 5,486,286 A | 1/1996 | Peterson et al. | |
| 5,487,827 A | 1/1996 | Peterson et al. | |
| 5,609,770 A | 3/1997 | Zimmerman et al. | |
| 5,618,441 A | 4/1997 | Rosa et al. | |
| 5,620,608 A | 4/1997 | Rosa et al. | |
| 5,634,896 A | 6/1997 | Bryant et al. | |
| 5,653,887 A | 8/1997 | Wahl et al. | 210/745 |
| 5,788,851 A | 8/1998 | Kenley et al. | |
| 5,858,239 A | 1/1999 | Kenley et al. | |
| 5,903,211 A | 5/1999 | Flego et al. | |
| 5,930,732 A | 7/1999 | Domanik et al. | |
| 5,989,423 A | 11/1999 | Kamen et al. | |
| 6,038,588 A | 3/2000 | Nagarajayya et al. | |
| 6,146,523 A | 11/2000 | Kenley et al. | |
| 6,198,698 B1 | 3/2001 | Graves | |
| 6,234,989 B1 | 5/2001 | Brierton et al. | |
| 6,284,131 B1 | 9/2001 | Hogard et al. | |
| 6,595,948 B2 | 7/2003 | Suzuki et al. | |
| 6,673,314 B1 | 1/2004 | Burbank et al. | |
| 6,764,761 B2 | 7/2004 | Eu et al. | |
| 6,773,412 B2 | 8/2004 | O'Mahony et al. | |
| 6,923,782 B2 | 8/2005 | O'Mahony et al. | |
| 6,979,309 B2 | 12/2005 | Burbank et al. | |
| 7,033,539 B2 | 4/2006 | Krensky et al. | |
| 7,264,730 B2 | 9/2007 | Connell et al. | |
| 7,303,680 B2 | 12/2007 | Connell et al. | |
| 7,318,892 B2 | 1/2008 | Connell et al. | |
| 7,351,340 B2 | 4/2008 | Connell et al. | |
| 7,410,475 B2 | 8/2008 | Krensky et al. | |
| 2002/0045851 A1 | 4/2002 | Suzuki et al. | |
| 2006/0113250 A1 | 6/2006 | Krensky et al. | |

OTHER PUBLICATIONS

Operator's Manual—Fresenius 2008K Hemodialysis Machine (2000).
Operator's Manual—Gambro Serena (Apr. 2002).
Operator Instructions Fresenius Hemodialysis Machine A2008D, Manual 500130 Rev. A, Seratronics, Inc., 1987.
Operator Instructions, Freedom™ Cycler PD+ IQcard™.
Baxter Home Choice, Patient At–Home Guide, 1994 (97 pgs.).
Operator Instructions, Fresenius Hemodialysis Machine 2008BSS, Manual 460001 Rev: B, 1990 and 1993, (56 pgs.).
Tina, System 1000 Brochure.
HD–Secura Operating Manual 1991 (B. Braun, 1991).
Sarns® 3M 9000 Perfusion System Operators Manual, Sarns 3M, Jan. 1989 [F298963–92.].
Fresenius, *CMS 08—Handbook*, Fresenius AG, 1988. [F330311–80.]—Part I, pp. 1–35; Part II, pp. 36–70.
Sturniolo, A., et al.,"Computerised Monitoring of Sodium and Fluid During Haemodialysis," Nephrological Dialysis and Transplant, Supplement 1, European Dialysis and Transplant Association—European Renal Association, 1990, (pp. 162–164).
Operating Instructions, Haemodialysis machine A 2008 D, 1989, (177 pgs.).

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 1, line 34–Column 2, line 33:

FIG. 1 shows a representation of a front control panel of a hemodialysis machine that incorporates the method and system for controlling multiple functions of a medical device with a single button of the present invention. Referring now to FIG. 1, in one embodiment of the invention, Front Control Panel [100] *100* is located at the top and front of a hemodialysis machine, such as the Fresenius 2008K Model made by Fresenius USA, Inc., that contains the control keys an operator needs to operate the hemodialysis machine. Keys with related functions are grouped into four sections on Front Control Panel 100. The General Operation Section 102 has control keys (not shown in FIG. 1) associated with starting or stopping the basic power and alarm aspects of a dialysis treatment. General Operation Section 102 has control keys for turning the power on, muting or silencing an alarm, selecting a new patient (which erases the treatment information of the previous patient), and a reset for resettting alarms and for setting new arterial, venous, and transmembrane pressure (TMP).

Treatment Display Section 104 is located in the middle of Front Control Panel 100 and has Graphics Display 110 that is overlain with Touch Screen 118. Graphics Display 110 can display a variety of treatment screens[through], which the operator can use to set treatment parameters and monitor the treatment. Graphics Display 110 may be a CRT or an LCD type display. Touch Screen 118 allows operator input to set the treatment parameters and monitor the treatment and patient status during dialysis. The operator can access different treatment screens and set treatment parameters by touching Touch Screen 118 at specific identified areas graphically displayed as images of buttons or keys on Graphics Display 110. The terms "button" and "key" are used interchangeably herein, and may represent a physical button or key, or represent a displayed image of a button or key. Both physical buttons or keys and displayed images of buttons or keys that receive operator touch input send signals that are interpreted by the electronics of the hemodialysis machine. The touch input from the operator on the specific identified areas on Touch Screen 118 send signals which actuate the display of different treatment screens and set the treatment parameters. In one embodiment, most numbers and parameters selected on Touch Screen 118, or actions initiated on Touch Screen 118, must be confirmed by pressing the Confirm Key 116, which sends a signal that must be received in order to enable the previous signal to have its desired effect. This feature prevents a change in a treatment value if the touch screen is accidentally bumped. Other embodiments do not require the use of Confirm Key 116. Escape Key 114 is used to void the current entry and return to the previously entered parameter value. The other physical keys for operator input besides Escape Key 114 and Confirm Key 116 are the keys in Keypad 112, which are the number keys 0–9 and an up arrow key and a down arrow key. The number keys in Keypad 112 may be used to enter treatment parameter values for such treatment options as utrafiltration rate, times, goal, and volumes, or for making selections inside a treatment screen displayed on Graphics Display 110. The up and down arrow keys may be used to scroll up or down a list of parameter choices or to increase or decrease parameter values. In another embodiment of the invention, Keypad 112, Escape Key 114, and Confirm Key 116 are graphically displayed as images of buttons or keys on Graphics Display 110 and actuated through Touch Screen 118. One skilled in the art will recognize that an infinite number of variations and combinations of physical buttons or keys and graphically displayed images of buttons or keys may be used in the present invention.

Column 3, lines 1–8:

Status Box 218 appears at the top left corner of every treatment screen. During normal operation it displays the operation mode of the machine, which in this case is ["Dialysis."During] *"Dialysis." During* alarm situations, a warning message is displayed in Status Box 218. The message displayed in Status Box 218 may also prompt the operator for a specific action in situations when the treatment parameters are being set.

Column 3, lines 27–49:

UF-Goal Button 238 displays the desired ultrafiltration (UF) in milliliters to be removed during the dialysis treatment. This is typically the difference between the patient's pre and dry weight plus saline or fluid intake during treatment. UF-Time Button 240 acts as a countdown timer displaying the remaining time in hours and minutes that ultrafiltration will be performed. The timer stops during a blood alarm or whenever the UF pump is stopped. During treatment, UF-Rate Button 242 displays the current rate of ultrafiltration in milliliters per hour. The rate *at which* ultrafiltration occurs is determined by the values entered in UF-Goal Button 238 and UF-Time Button 240 and the profile selected with UF-Profile Button 246. UF-Removed Button 244 keeps a running total in milliliters of the fluid drawn from the patient through ultrafiltration. When the value displayed in UF-Removed Button 244 is equal to the value entered in UF-Goal Button 238, an alarm sounds and the message, "UF GOAL REACHED" is displayed in Status Box 218. UF-Profile Button 246 when touched brings up the UF Profile Selection Screen. Once a profile is selected, and the operator pushes Home Access Button 202, the profile selected is displayed in UF-Profile Button 246.

AS A RESULT OF REEXAMINATION, IT HAS BEEN DETERMINED THAT:

The patentability of claims 4, 19, 33, 37, 41, 42, 46 and 59 is confirmed.

Claims 1–3, 6, 14, 21, 26, 31, 35, 36, 39, 40, 43, 48 and 57 are cancelled.

Claims 5, 7, 11, 15–18, 20, 22, 25, 27, 32, 34, 38, 44, 45, 47, 49, 51, 52, 54, 58 and 60 are determined to be patentable as amended.

Claims 8, 9, 10, 12, 13, 23, 24, 28–30, 50, 53, 55 and 56, dependent on an amended claim, are determined to be patentable.

New claims 61–134 are added and determined to be patentable.

5. A method according to claim [1] *73* wherein said button comprises a button image displayed on a graphics display of the medical device, wherein said graphics display is overlain with a touch screen for receiving touch input from an operator, such as said first operator input on said button image displayed on said graphics display.

7. A method according to claim 6 further comprising:
receiving a second operator on said button, wherein said second operator input on said button actuates,
displaying graphically on said graphics display a pause of said progress of treatment time;
*pausing said first alarm function and* enabling a second alarm function of the medical device; and
*pausing said first control function and* enabling a second control function of the medical device.

11. A method according to claim [6] *115* wherein said displaying graphically said progress of treatment time further comprises:
displaying a time remaining segment in a first color that proportionally decreases in area as said progress of treatment time elapses; and
displaying a time elapsed segment in a second color that proportionally increases in area as said progress of treatment time elapses.

15. A method according to claim [14] *116* wherein said first alarm function further comprises sounding an audible alarm if no blood is sensed in a blood circuit of said hemodialysis machine when said progress of treatment time is graphically displayed as running.

16. A method according to claim [14] *116* wherein said first control function further comprises allowing automatic blood pressure measurements when said progress of treatment time is graphically displayed as running.

17. A method according to claim [14] *7* wherein *the medical device comprises a hemodialysis machine and* said second alarm function further comprises sounding an audible alarm if blood is sensed in a blood circuit of said hemodialysis machine when said progress of treatment time is graphically displayed as paused.

18. A method according to claim [14] *116* wherein said at least one function of said hemodialysis machine comprises at least one of an ultrafiltration pump, a blood pump, a blood pressure detector, a heparin pump, a level detector, and a dialyzer.

20. A method according to claim [14] *116* wherein said at least two parameters of said hemodialysis machine comprise at least two of a Kt/V, a blood temperature, an ultrafiltration volume accumulated, a heparin volume accumulated, a blood pressure, a blood volume processed, and a clearance test.

22. The system according to claim [21] *75* wherein [a] *the* second operator input signal is interpreted by said processor and *the processor* outputs a second plurality of control signals that,
suspend at least one of said at least one component of the medical device;
suspend at least one of said at least two time accumulations of the medical device; and
suspend said accumulation of at least one of said at least two parameters of the medical device.

25. The system according to claim [21] *75* further comprising:
a graphics display of the medical device in communication with said processor;
a touch screen overlaying said graphics display in communication with said processor for receiving touch input from an operator;
wherein said program code further comprises,
a touch screen controller; and
a user interface;
wherein said button comprises a button image displayed on said graphics display of the medical device, wherein said touch screen receives touch input from an operator, such as said first operator input on said button image displayed on said graphics display, and sends said operator input signal.

27. The system according to claim 26 wherein a second operator input signal interpreted by said processor outputs a second plurality of control signals that,
cause said graphics display to display graphically a pause of said progress of treatment time;
*pause said first alarm function and* enable a second alarm function of the medical device; and
*pause said first control function and* enable a second control function of the medical device.

32. The system according to claim [31] *118* wherein said at least one component of said hemodialysis machine comprises at least one of an ultrafiltration pump, a blood pump, a blood pressure detector, a heparin pump, a level detector, and a dialyzer.

34. The system according to claim [31] *118* wherein said at least two parameters of said hemodialysis machine comprise at least two of a Kt/V, a blood temperature, an ultrafiltration volume accumulated, a heparin volume accumulated, a blood pressure, a blood volume processed, and a clearance test.

38. A method according to claim [35] *77* wherein said button comprises a button image displayed on a graphics display of the medical device, wherein said graphics display is overlain with a touch screen for receiving touch input from an operator, such as said operator input on said button image displayed on said graphics display.

44. A method according to claim 43 wherein said [second] alarm function further comprises sounding an audible alarm if blood is sensed in a blood circuit of said hemodialysis machine when said progress of treatment time is graphically displayed as paused.

45. A method according to claim [43] *122* wherein said at least one function of said hemodialysis machine comprises at least one of an ultrafiltration pump, a blood pump, a blood pressure detector, a heparin pump, a level detector, and a dialyzer.

47. A method according to claim [43] *122* wherein said at least two parameters of said hemodialysis machine comprises at least two of a Kt/V, a blood temperature, an ultrafiltration volume accumulated, a heparin volume accumulated, a blood pressure, a blood volume processed, and a clearance test.

49. The system according to claim [48] *78* wherein [a] *the* next operator input signal after said operator input signal is interpreted by said processor and *the processor* outputs a next plurality of control signals that,
resume said suspended said at least one of said at least one component of the medical device;
resume said suspended at least one of said at least two time accumulations of the medical device; and
resume said suspended said accumulation of at least one of said at least two parameters of the medical device.

51. The system according to claim [48] *78* further comprising:
a graphics display of the medical device in communication with said processor;
a touch screen overlaying said graphics display in communication with said processor;

wherein said program code further comprises,
a touch screen controller; and
a user interface;
wherein said button comprises a button image displayed on said graphics display of the medical device, wherein said touch screen receives touch input from an operator, such as said [first] operator input on said button image displayed on said graphics display, and sends said operator input signal.

52. The system according to claim [48] *78* further comprising:
a graphics display of the medical device in communication with said processor.

54. The system according to claim 53 wherein [a] *the* next operator input signal after said operator input signal is interpreted by said processor and *the processor* outputs a next plurality of control signals that,
cause said graphics display to display graphically a resumption in said progress of treatment time;
enable a second alarm function of the medical device; and
enable a second control function of the medical device.

58. The system according to claim [57] *123* wherein said at least one component of said hemodialysis machine comprises at least one of an ultrafiltration pump, a blood pump, a blood pressure detector, a heparin pump, a level detector, and a dialyzer.

60. The system according to claim [57] *123* wherein said at least two parameters of said hemodialysis machine comprise at least two of a Kt/V, a blood temperature, an ultrafiltration volume accumulated, a heparin volume accumulated, a blood pressure, a blood volume processed, and a clearance test.

*61. The method according to claim 73, wherein said at least one function of said medical device comprises running of an ultrafiltration pump and running of a heparin pump, said at least two time accumulations of said medical device comprise an ultrafiltration time and a heparin pump time, and said at least two parameters of said medical device comprise an ultrafiltration volume accumulated and a heparin volume accumulated.*

*62. The system according to claim 75, wherein said at least one component of said medical device comprises an ultrafiltration pump and a heparin pump, said at least two time accumulations of said medical device comprise an ultrafiltration time and a heparin pump time, and said at least two parameters of said medical device comprise an ultrafiltration volume accumulated and a heparin volume accumulated.*

*63. The method according to claim 77, wherein said at least one function of said medical device comprises running of an ultrafiltration pump and running of a heparin pump, said at least two time accumulations of said medical device comprise an ultrafiltration time and a heparin pump time, and said at least two parameters of said medical device comprise an ultrafiltration volume accumulated and a heparin volume accumulated.*

*64. The system according to claim 78, wherein said at least one component of said medical device comprises an ultrafiltration pump and a heparin pump, said at least two time accumulations of said medical device comprise an ultrafiltration time and a heparin pump time, and said at least two parameters of said medical device comprise an ultrafiltration volume accumulated and a heparin volume accumulated.*

*65. The method according to claim 73, wherein said at least one function of said medical device comprises running of an ultrafiltration pump.*

*66. The system according to claim 75, wherein said at least one component of said medical device comprises an ultrafiltration pump.*

*67. The method according to claim 77, wherein said at least one function of said medical device comprises running of an ultrafiltration pump.*

*68. The system according to claim 78, wherein said at least one component of said medical device comprises an ultrafiltration pump.*

*69. The method according to claim 73, wherein said at least one function of said medical device comprises running of a heparin pump.*

*70. The system according to claim 75, wherein said at least one component of said medical device comprises a heparin pump.*

*71. The method according to claim 77, wherein said at least one function of said medical device comprises running of a heparin pump.*

*72. The system according to claim 78, wherein said at least one component of said medical device comprises a heparin pump.*

*73. A method for controlling multiple functions of a medical device, the method comprising:
receiving a first operator input on a button of the medical device, wherein said first operator input on said button actuates,
starting at least one function of the medical device;
starting at least two time accumulations of the medical device; and
starting accumulation of at least two parameters of the medical device; and
receiving a second operator input on said button, wherein a blood pump of said medical device remains running after said second operator input on said button.*

*74. The method according to claim 73, wherein running of the blood pump is not a function of the medical device that is started when the first operator input is received on the button.*

*75. A system for controlling multiple functions of a medical device, the system comprising:
a button for receiving operator input and sending an operator input signal;
a processor, connectable to said button for receiving said operator input signal, said processor having,
a memory; and
a program code stored in said memory;
wherein said processor running said program code interprets said operator input signal and outputs control signals; and
at least one component of the medical device in communication with said processor;
wherein a first operator input signal is interpreted by said processor and outputs a first plurality of control signals that,
start said at least one component of the medical device;
start at least two time accumulations of the medical device; and,
start accumulation of at least two parameters of the medical device, and
wherein a second operator input signal is sent to said processor by said button, and, in response to said second operator input signal, said processor maintains a blood pump of said medical device in a running state.*

*76. The system according to claim 75, wherein the blood pump is not a component of the medical device that is started when the processor outputs the first plurality of control signals.*

77. A method for controlling multiple functions of a medical device, the method comprising:
receiving an operator input on a button of the medical device, wherein said operator input on said button actuates,
suspending at least one of at least one function of the medical device;
suspending at least one of at least two time accumulations of the medical device; and
suspending accumulation of at least one of at least two parameters of the medical device,
wherein a blood pump of said medical device remains running after said operator input on said button.

78. A system for controlling multiple functions of a medical device, the system comprising:
a button for receiving operator input and sending an operator input signal;
a processor, connectable to said button for receiving said operator input signal, said processor having,
a memory; and
a program code stored in said memory;
wherein said processor running said program code interprets said operator input signal and outputs control signals; and
at least one component of the medical device in communication with said processor;
wherein an operator input signal is interpreted by said processor and outputs a plurality of control signals that,
suspend at least one of said at least one component of the medical device;
suspend at least one of at least two time accumulations of the medical device; and
suspend accumulation of at least one of at least two parameters of the medical device, and
wherein a next operator input signal is sent to said processor by said button, and, in response to said next operator input signal, said processor maintains a blood pump of said medical device in a running state.

79. The method according to claim 73, wherein said medical device is a hemodialysis machine, and said first operator input on said button further enables an alarm to emit a signal if blood is not sensed in an extracorporeal circuit of said hemodialysis machine.

80. The method according to claim 79, wherein said second operator input on said button actuates suspending at least one of said at least one function and enabling a second alarm to emit a signal if blood is sensed in said extracorporeal circuit of said hemodialysis machine when said at least one function is suspended.

81. The system according to claim 75, wherein said medical device is a hemodialysis machine, said first operator input signal is sent to said processor by said button, and, in response to said first operator input signal, said processor enables an alarm to emit a signal if blood is not sensed in an extracorporeal circuit of said hemodialysis machine.

82. The system according to claim 81, wherein, in response to said second operator input signal, said processor suspends at least one of said at least one component and enables a second alarm to emit a signal if blood is sensed in said extracorporeal circuit of said hemodialysis machine when said at least one component is suspended.

83. The method according to claim 77, wherein said medical device is a hemodialysis machine, and said operator input on said button enables an alarm adapted to emit a signal if blood is sensed in an extracorporeal circuit of said hemodialysis machine when said at least one function is suspended.

84. The method according to claim 83, further comprising receiving a next operator input on said button, wherein said next operator input on said button actuates resuming at least one of said at least one function and enables a second alarm to emit a signal if blood is not sensed in said extracorporeal circuit of said hemodialysis machine.

85. The system according to claim 78, wherein said medical device is a hemodialysis machine, said operator input signal interpreted by said processor is sent to said processor by said button, and, in response to said operator input signal interpreted by said processor, said processor enables an alarm to emit a signal if blood is sensed in an extracorporeal circuit of said hemodialysis machine when said at least one component is suspended.

86. The system according to claim 85, wherein, in response to said next operator input signal, said processor actuates resuming at least one of said at least one component and enables a second alarm to emit a signal if blood is not sensed in said extracorporeal circuit of said hemodialysis device.

87. The system according to claim 75, wherein said first operator input signal is sent to said processor by said button, and, in response to said first operator input signal, said processor outputs said first plurality of control signals.

88. The system according to claim 87, wherein, in response to said second operator input signal, said processor outputs a second plurality of control signals that,
suspend at least one of said at least one component of the medical device;
suspend at least one of said at least two time accumulations of the medical device; and
suspend said accumulation of at least one of said at least two parameters of the medical device.

89. The system according to claim 88, wherein a third operator input signal sent to said processor by said button is interpreted by said processor, and, in response to said third operator input signal, said processor outputs a third plurality of control signals that,
resume said suspended said at least one of said at least one component of the medical device;
resume said suspended at least one of said at least two time accumulations of the medical device; and
resume said suspended said accumulation of at least one of said at least two parameters of the medical device.

90. The system according to claim 78, wherein said operator input signal interpreted by said processor is sent to said processor by said button, and, in response to said operator input signal interpreted by said processor, said processor outputs said plurality of control signals.

91. The system according to claim 90, wherein, in response to said next operator input signal, said processor outputs a next plurality of control signals that,
resume said suspended said at least one of said at least one component of the medical device;
resume said suspended at least one of said at least two time accumulations of the medical device; and
resume said suspended said accumulation of at least one of said at least two parameters of the medical device.

92. The method according to claim 116, wherein said first control function further comprises enabling automatic blood pressure measurements when said progress of treatment time is graphically displayed as running.

93. The method according to claim 116, wherein said at least one function of said hemodialysis machine comprises at least one function of an ultrafiltration pump, a blood pressure detector, a heparin pump, a level detector or a dialyzer.

94. The method according to claim 122, wherein said at least one function of said hemodialysis machine comprises at least one function of an ultrafiltration pump, a blood pressure detector, a heparin pump, a level detector or a dialyzer.

95. The method according to claim 4, wherein said button has a perimeter region adapted to change from a first color to a second color after the confirm key is pressed.

96. The system according to claim 24, wherein said button has a perimeter region adapted to change from a first color to a second color after the confirm key is pressed.

97. The method according to claim 37, wherein said button has a perimeter region adapted to change from a first color to a second color after the confirm key is pressed.

98. The system according to claim 50, wherein said button has a perimeter region adapted to change from a first color to a second color after the confirm key is pressed.

99. The system according to claim 23 further comprising:
a confirm key connectable to said processor for receiving operator confirm input and sending an operator confirm input signal,
wherein said processor is adapted so that said output control signals associated with said first operator input signal, said second operator input signal, and said third operator input signal must be followed by said operator confirm input signal before said output control signals are output by said processor.

100. The system according to claim 28, wherein said processor is adapted so that said output control signals associated with said first operator input signal, said second operator input signal, and said third operator input signal must be followed by said operator confirm input signal before said output control signals are output by said processor.

101. The system according to claim 49 further comprising:
a confirm key connectable to said processor for receiving operator confirm input and sending an operator confirm input signal,
wherein said processor is adapted so that said output control signals associated with said operator input signal and said next operator input signal must be followed by said operator confirm input signal before said output control signals are output by said processor.

102. The system according to claim 54 wherein said processor is adapted so that said output control signals associated with said operator input signal and said next operator input signal must be followed by said operator confirm input signal before said output control signals are output by said processor.

103. The method according to claim 73, wherein said first operator input must be followed by an operator confirm key input before actuation occurs.

104. The method according to claim 113, wherein said second operator input must be followed by an operator confirm key input before actuation occurs.

105. The method according to claim 114, wherein said third operator input must be followed by an operator confirm key input before actuation occurs.

106. The system according to claim 75 further comprising:
a confirm key connectable to said processor for receiving operator confirm input and sending an operator confirm input signal,
wherein said processor is adapted so that said output control signals associated with said first operator input signal must be followed by said operator confirm input signal before said output control signals are output by said processor.

107. The system according to claim 22 further comprising:
a confirm key connectable to said processor for receiving operator confirm input and sending an operator confirm input signal,
wherein said processor is adapted so that said second plurality of output control signals associated with said second operator input signal must be followed by said operator confirm input signal before said second plurality of output control signals are output by said processor.

108. The system according to claim 23 further comprising:
a confirm key connectable to said processor for receiving operator confirm input and sending an operator confirm input signal,
wherein said processor is adapted so that said third plurality of output control signals associated with said third operator input signal must be followed by said operator confirm input signal before said third plurality of output control signals are output by said processor.

109. The method according to claim 77, wherein said operator input must be followed by an operator confirm key input before actuation occurs.

110. The method according to claim 119, wherein said next operator input must be followed by an operator confirm key input before acutation occurs.

111. The system according to claim 78 further comprising:
a confirm key connectable to said processor for receiving operator confirm input and sending an operator confirm input signal,
wherein said processor is adapted so that said plurality of output control signals associated with said operator input signal must be followed by said operator confirm input signal before said plurality of output control signals are output by said processor.

112. The system according to claim 49 further comprising:
a confirm key connectable to said processor for receiving operator confirm input and sending an operator confirm input signal,
wherein said processor is adapted so that said next plurality of output control signals associated with said next operator input signal must be followed by said operator confirm input signal before said next plurality of output control signals are output by said processor.

113. A method according to claim 73 wherein said second operator input on said button actuates,
suspending at least one of said at least one function of the medical device;
suspending at least one of said at least two time accumulations of the medical device; and
suspending said accumulation of at least one of said at least two parameters of the medical device.

114. A method according to claim 113, further comprising:
receiving a third operator input on said button, wherein said third operator input on said button actuates,
resuming said suspended said at least one of said at least one function of the medical device;
resuming said suspended said at least one of said at least two time accumulations of the medical device; and
resuming said suspended said accumulation of at least one of said at least two parameters of the medical device.

115. A method according to claim 73 wherein said first operator input on said button further actuates:
- displaying graphically on a graphics display of the medical device a progress of treatment time;
- enabling a first alarm function of the medical device; and
- enabling a first control function of the medical device.

116. A method according to claim 115 wherein the medical device comprises a hemodialysis machine.

117. The system according to claim 75 further comprising:
- a graphics display of the medical device in communication with said processor;
- wherein said first plurality of control signals additionally, cause said graphics display to display graphically a progress of treatment time;
- enable a first alarm function of the medical device; and
- enable a first control function of the medical device.

118. The system according to claim 75 wherein the medical device comprises a hemodialysis machine.

119. A method according to claim 77 further comprising:
- receiving a next operator input on said button after said operator input, wherein said next operator input on said button actuates,
  - resuming said suspended said at least one of said at least one function of the medical device;
  - resuming said suspended said at least one of said at least two time accumulations of the medical device; and
  - resuming said suspended said accumulation of at least one of said at least two parameters of the medical device.

120. A method according to claim 77 wherein said operator input on said button further actuates:
- displaying graphically on a graphics display of the medical device a pause in a progress of treatment time;
- enabling an alarm function of the medical device; and
- enabling a control function of the medical device.

121. A method according to claim 120 further comprising:
- receiving a next operator input on said button after said operator input, wherein said next operator input on said button actuates,
  - displaying graphically on said graphics display a resumption in said progress of treatment time;
  - enabling a second alarm function of the medical device; and
  - enabling a second control function of the medical device.

122. A method according to claim 120 wherein the medical device comprises a hemodialysis machine.

123. The system according to claim 78 wherein the medical device comprises a hemodialysis machine.

124. A method for controlling multiple functions of a medical device, the method comprising:
- receiving a first operator input on a button of the medical device, wherein said first operator input on said button actuates,
  - starting at least one function of the medical device;
  - starting at least two time accumulations of the medical device; and
  - starting accumulation of at least two parameters of the medical device, and
- wherein said first operator input must be followed by an operator confirm key input before actuation occurs.

125. A method according to claim 124 further comprising:
- receiving a second operator input on said button, wherein said second operator input on said button actuates,
  - suspending at least one of said at least one function of the medical device;
  - suspending at least one of said at least two time accumulations of the medical device; and
  - suspending said accumulation of at least one of said at least two parameters of the medical device.

126. The method according to claim 125, wherein said second operator input must be followed by an operator confirm key input before actuation occurs.

127. A method according to claim 125 further comprising:
- receiving a third operator input on said button, wherein said third operator input on said button actuates,
  - resuming said suspended said at least one of said at least one function of the medical device;
  - resuming said suspended said at least one of said at least two time accumulations of the medical device; and
  - resuming said suspended said accumulation of at least one of said at least two parameters of the medical device.

128. The method according to claim 127, wherein said third operator input must be followed by an operator confirm key input before actuation occurs.

129. The method according to claim 124, wherein said at least one function of said medical device comprises running of an ultrafiltration pump and running of a heparin pump, said at least two time accumulations of said medical device comprise an ultrafiltration time and a heparin pump time, and said at least two paramters of said medical device comprise an ultrafiltration volume accumulated and a heparin volume accumulated.

130. The method according to claim 124, wherein said at least one function of said medical device comprises running of an ultrafiltration pump.

131. The method according to claim 124, wherein said at least one function of said medical device comprises running of a heparin pump.

132. The method according to claim 124, wherein said medical device is a hemodialysis machine, and said first operator input on said button further enables an alarm to emit a signal if blood is not sensed in an extracorporeal circuit of said hemodialysis machine.

133. The method according to claim 132, further comprising receiving a second operator input on said button, wherein said second operator input on said button actuates suspending at least one of said at least one function and enabling a second alarm to emit a signal if blood is sensed in said extracorporeal circuit of said hemodialysis machine when said at least one function is suspended.

134. A method for controlling multiple functions of a medical device, the method comprising:
- receiving an operator input on a button of the medical device, wherein said operator input on said button actuates,
  - suspending at least one of at least one function of the medical device;
  - suspending at least one of at least two time accumulations of the medical device; and
  - suspending accumulation of at least one of at least two parameters of the medical device,
- wherein said operator input must be followed by an operator confirm key input before actuation occurs.

* * * * *